(12) United States Patent
Malawer

(10) Patent No.: US 6,641,615 B2
(45) Date of Patent: Nov. 4, 2003

(54) ACETABULUM SPACING DEVICE

(76) Inventor: Martin M. Malawer, 913 Frome La., McLean, VA (US) 22102

( * ) Notice: Subject to any disclaimer, the term of this patent is extended or adjusted under 35 U.S.C. 154(b) by 0 days.

(21) Appl. No.: 09/985,567

(22) Filed: Nov. 5, 2001

(65) Prior Publication Data

US 2002/0026245 A1 Feb. 28, 2002

Related U.S. Application Data (62) Division of application No. 09/644,705, filed on Aug. 24, 2000, now Pat. No. 6,312,470, which is a division of application No. 09/073,188, filed on May 6, 1998, now abandoned.

(51) Int. Cl.$^7$ .................................................. A61F 2/30
(52) U.S. Cl. ................................. 623/18.11; 623/22.11
(58) Field of Search ........................... 623/17.16, 18.11, 623/21.11, 22.21, 19.11, 21.16, 16.11; 606/81, 61, 74

(56) References Cited

U.S. PATENT DOCUMENTS

| | | |
|---|---|---|
| 3,840,904 A | 10/1974 | Tronzo |
| 4,285,071 A | 8/1981 | Nelson et al. |
| 4,936,848 A | 6/1990 | Bagby |
| 5,007,936 A | 4/1991 | Woolson |
| 5,282,861 A | 2/1994 | Kaplan |
| 5,326,367 A | 7/1994 | Robloneck |
| 5,344,458 A | 9/1994 | Bonutti |
| 5,425,777 A | 6/1995 | Sarkisian et al. |
| 5,458,643 A | 10/1995 | Oka et al. |
| 5,507,827 A | 4/1996 | Grundei et al. |
| 5,514,184 A | 5/1996 | Doi et al. |
| 5,609,646 A | 3/1997 | Field et al. |
| 5,658,347 A | 8/1997 | Sarkisian et al. |
| 5,728,163 A * | 3/1998 | Maksene ..................... 623/21 |
| 5,749,875 A | 5/1998 | Puddu |
| 5,769,899 A | 6/1998 | Schwartz et al. |

FOREIGN PATENT DOCUMENTS

JP 5-200058 A 8/1993

* cited by examiner

*Primary Examiner*—Bruce Snow
(74) *Attorney, Agent, or Firm*—Nixon & Peabody LLP; Donald R. Studebaker (57) ABSTRACT

A spacing device for supporting a joint adjacent to diseased bone or missing bone tissue, comprising a support piece and a semi-resilient pad. The pad is shaped to cradle and support the healthy bone joint. The reverse side of the pad is fixedly connected to one end of the support piece. The other end of the support piece is shaped to straddle healthy tissue adjacent the damaged area, such as the ilium when supporting a hip joint and is to be fixedly connected to the adjacent healthy tissue, using a suitable mechanism, such as biocompatible Steinman pins. Diseased, damaged, or necrotic tissue can be removed without requiring removal of the natural bone joint. Because the undamaged bone joint is not replaced, the problems commonly experienced during and following bone joint replacement are avoided. In particular, blood loss during surgery, surgical cost, surgical time, and rehabilitation of the patient after surgery is reduced. The method of implanting the spacer for supporting a bone joint includes the steps of exposing the joint; curetting damaged tissue from the bone; selecting an appropriately sized spacer for the joint; inserting the spacer into position adjacent healthy bone tissue and the joint; seating the spacer in an appropriate position; and fixedly securing the spacer in the position.

6 Claims, 7 Drawing Sheets

ACETABULUM SPACING DEVICE

This application is a Divisional of U.S. application Ser. No. 09/644,705 filed Aug. 24, 2000, now U.S. Pat. No. 6,312,470 which is a Divisional of U.S. application Ser. No. 09/073,188 filed May 6, 1998, now abandoned.

TECHNICAL FIELD

The present invention is directed generally to devices that can be inserted into the body in place of damaged bone tissue to provide underlying support for bone joints, without requiring complete or even partial replacement of the bone joint.

BACKGROUND OF THE INVENTION

Endoprostheses have been commonly used to replace the damaged ball of the femur and/or the acetabular socket of the hip bone when these parts are damaged or deteriorate and do not properly function. In cancer-damaged hip bones, a portion of the pelvis (ilium) is attacked by cancer and is thus incapable of supporting the acetabulum in the usual manner. While a hip replacement is not necessitated due to failure of the femoral ball or the acetabulum, it is commonly performed in such a situation because there has been no way to preserve the acetabulum cup while removing the damaged tissue from the pelvis beneath, and supporting the natural acetabulum to withstand the forces to which it is commonly subject. The acetabulum cup has routinely been removed prior to tissue removal and completely replaced with an artificial prosthesis after removal of the damaged pelvic tissue below.

Heretofore, total hip prosthesis surgery has been performed wherein a cup is fitted in the acetabulum, and a femoral prosthesis member, which comprises a stem or shank portion and an artificial head, is fixed to the femur to provide a prosthetic hip joint. Subtotal hip replacement formerly necessitated by the above-described pelvic damage has involved removal and replacement of the acetabulum with a metal acetabular cup, wherein the metal cup provides a metal-surfaced socket for receiving the head of the femur.

Total and subtotal hip replacement is undesirable in cases of pelvic damage where the natural ball and socket of the hip joint is undamaged. A significant number of total or subtotal hip joint implants have failed by the acetabular prosthesis coming loose from its mount. A loose acetabulum prosthesis can erode bone in the direction of the applied forces during use, i.e., in the superior and posterior directions. This is particularly true where the loosened prosthesis had been implanted using bone cement, polymethylmethacrylate (PMMA), and/or screws and pins. This accelerated erosion shortens the life of the implant.

While the prior art has addressed improvements in the field of bone joint replacement, it has not addressed the problem of unnecessarily removing healthy bone joints only because the support structure under the bone joint was diseased or damaged. For example, U.S. Pat. No. 5,326,367 to Robioneck discloses an endoprostheses for a cancer-damaged pelvis. The endoprostheses comprises distal and proximal parts that can be screwed together, and include mounting extensions to be screwed to the hip bone, or alternatively, to a vertebra. However, while Robioneck discloses a potentially viable device and method to implant a prosthesis in a damaged pelvis, it does not address the issue of how to support the bone joint without replacing it with an artificial prosthesis.

Consequently, there is a need for joint preservation rather than routine joint removal and replacement when only a portion of the pelvic bone is destroyed. Thus, a need exists for a device that can be inserted into the body in place of damaged bone tissue that provide underlying support for bone joints, preempting the requirement for complete or partial replacement of the bone joint, and methods for inserting such devices. Furthermore, the following device and method is likewise suitable for other joints within the human body.

SUMMARY OF INVENTION

It is a primary object of the present invention, therefore, to overcome the disadvantages of the prior art and provide a durable, reliable spacing device that can support a joint in a damaged bone so that replacement of the joint is not required.

It is a further object of the present invention to provide a method to implant such a spacing device.

A further object of the present invention is to reduce surgical time for the removal of damaged bone tissue adjacent to a joint previously requiring complete reconstruction of the socket portion of the joint.

A still further object of the present invention is to reduce blood loss by up to 80% over prior procedures by incorporating the above-noted surgical procedure in place of previously partial or full bone joint reconstruction. Additionally, surgical time and surgical complexity are significantly reduced.

Yet another object of the present invention is to decrease a patient's rehabilitation time by eliminating the necessity of partial or full bone joint reconstruction when removing diseased bone tissue adjacent to a joint.

The aforesaid objects are achieved by providing a spacing device for supporting a bone joint adjacent diseased or missing bone tissue, comprising a rigid support having a contoured surface and a semi-resilient pad. The pad is shaped to cradle and support the healthy bone joint and may promote bone integration. The reverse side of the pad is fixedly connected to one end of the contoured support piece. The other end of the contoured support piece is shaped to straddle healthy bone tissue adjacent the damaged area, such as the ilium in the case of a hip joint and is to be fixedly connected to the adjacent healthy tissue, using suitable means, such as biocompatible Steinman pins and polymethylmethacrylate (PMMA, bone cement). Other configurations of the support piece can be utilized depending on the joint needing support.

The result is that the diseased, damaged, or necrotic tissue can be removed without requiring removal of the natural bone joint. Because the undamaged bone joint is not replaced, the problems commonly experienced during an following bone joint replacement are avoided. In particular, blood loss during surgery, surgical cost, surgical time, and rehabilitation of the patient after surgery is reduced.

Other objects and advantages of the present invention will become apparent from the following detailed description when read in the light of the several figures.

DETAILED DESCRIPTION OF THE PRESENT INVENTION

In order for a bone joint, such as a hip, to function properly, it must be adequately supported from behind. Cancer and disease can cause necrosis or seriously damage the pelvis, rendering the natural support for the hip joint inadequate. Ideally, and in accordance with the present invention, the dead or diseased portion of the pelvis is removed without removing either all or part of the hip joint, and a support is placed behind the hip to lend adequate support to the joint. However, following removal of the dead or diseased portion of the pelvic bone, the typical procedure heretofore has been to remove at least the acetabulum, as well as a portion of the pelvis, and implant an artificial prosthesis. The present invention provides a time-saving and blood loss-reducing procedure for supporting the bone joint without requiring replacement of the joint, thus significantly reducing the patient's rehabilitation time.

While the following description is primarily directed to the hip joint region of the human body, it should be appreciated that other joints within the body may benefit in a similar manner from the procedure and device set forth hereinbelow.

Figure 1:
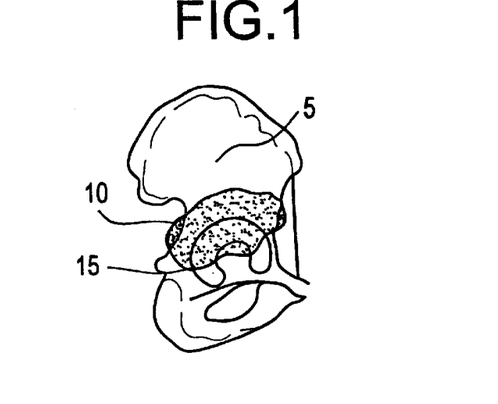
FIG. 1 is a view of a typical cancerous pelvic region, including an intact acetabular cartilage surface.

Referring to the drawings, FIG. 1 is a view of a typical cancerous pelvic region, including an intact acetabulum. The ilium (pelvis) 5 is the large bone, having a large cancer in contact with the cartilage (cartilage is rarely attacked or destroyed by cancer), which in turn supports the acetabulum 15. In this view, the cancer has spread to the ilium 5, but has not spread within the acetabulum 15 (hip joint space).

Figure 2:
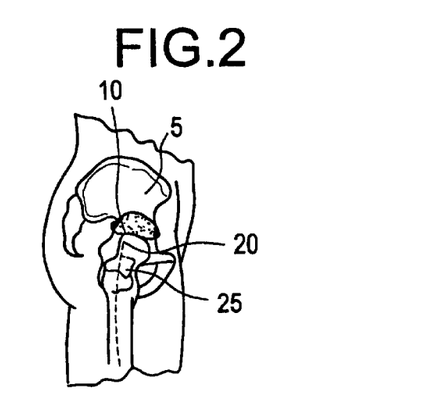
FIG. 2 illustrates the incision to take place for the acetabular spacing device to be inserted into a hip joint.
Figure 3:
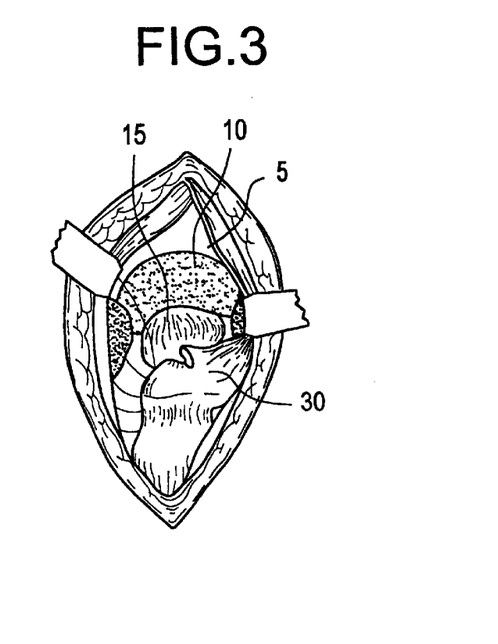
FIG. 3 is a view of the incision, showing the tumor, the abductor muscle, and the acetabulum.

FIG. 2 illustrates the incision area required for insertion of an acetabular spacing device into the hip in accordance with the present invention. The exposure of the hip joint area is via an incision 20 through a posterior lateral approach. This view shows the relative location of the ilium 5, the cartilage, and the femur 25. Once the location of the incision is determined, the incision 20 is carried out to expose the cancerous bone tissue 10, the abductor muscle 30, and the acetabulum 15, as shown in FIG. 3. The abductor muscle 30 is retracted anteriorly to expose the ilium 5 and the cancerous bone tissue 10 above the acetabulum 15. The cancerous bone tissue or tumor 10 is best visualized as a bulging of the cortex. Once the diseased area is determined, the tissue can be removed.

Figure 4:
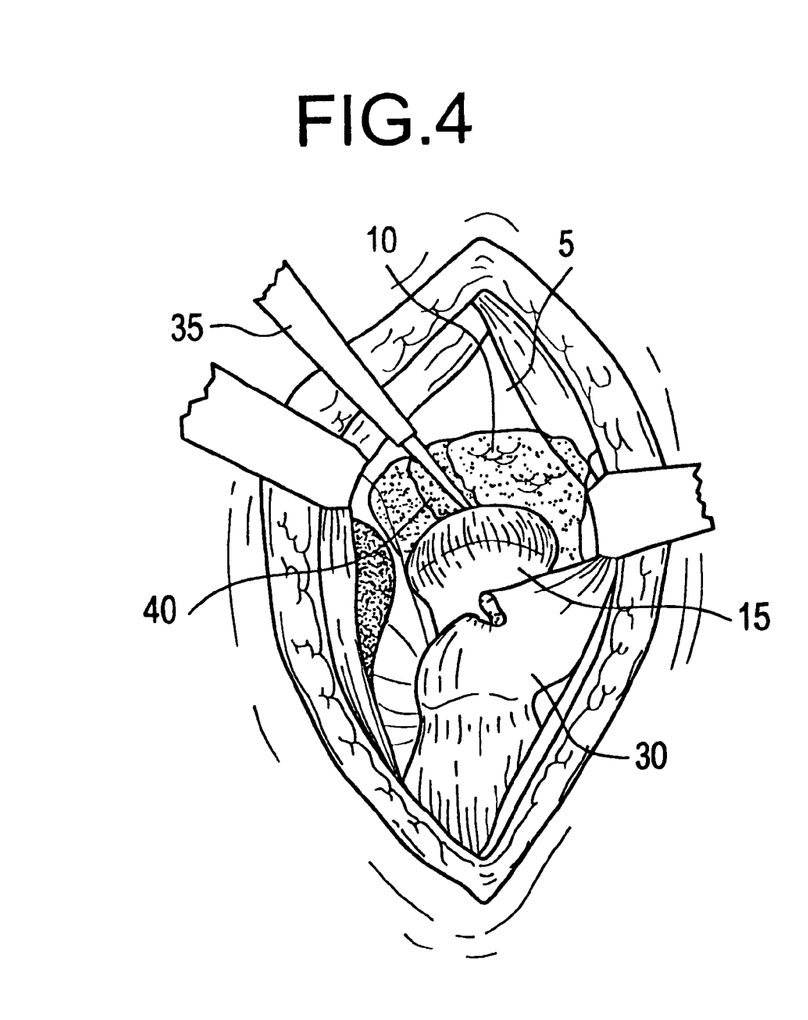
FIG. 4 illustrates the process of curetting of the tumor from the pelvis being carried out in accordance with the present invention.
Figure 5:
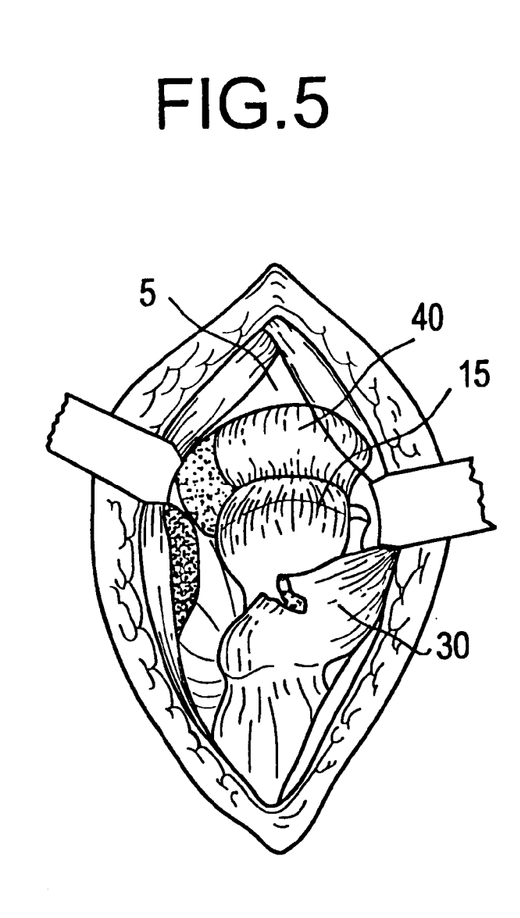
FIG. 5 illustrates the formerly cancerous pelvic area, cleaned and prepared for the insertion of the spacing device in accordance with the present invention.

FIG. 4 illustrates the curetting of the cancerous bone tissue 10 from the ilium 5. This step is accomplished with curettes 35 and power drills. Removing the cancerous material 10 creates a void 40 with the inner wall being the iliacus muscle and lower wall being the subchondular bone and articular cartilage of the hip joint. It is important to note that in accordance with the present invention, the hip joint is never actually entered. Once the diseased tissue is curetted from the area, the area is inspected to ensure complete removal of the diseased tissue. FIG. 5 illustrates the void 40 of the formerly cancerous pelvic area, cleaned and prepared for the insertion of an acetabular spacing device 45 in accordance with the present invention. As can be appreciated from FIG. 5, the acetabulum 15 is left fully intact and is not invaded in any way. Moreover, the ball portion of the hip joint remains in place received within the acetabulum 15.

Figure 6:
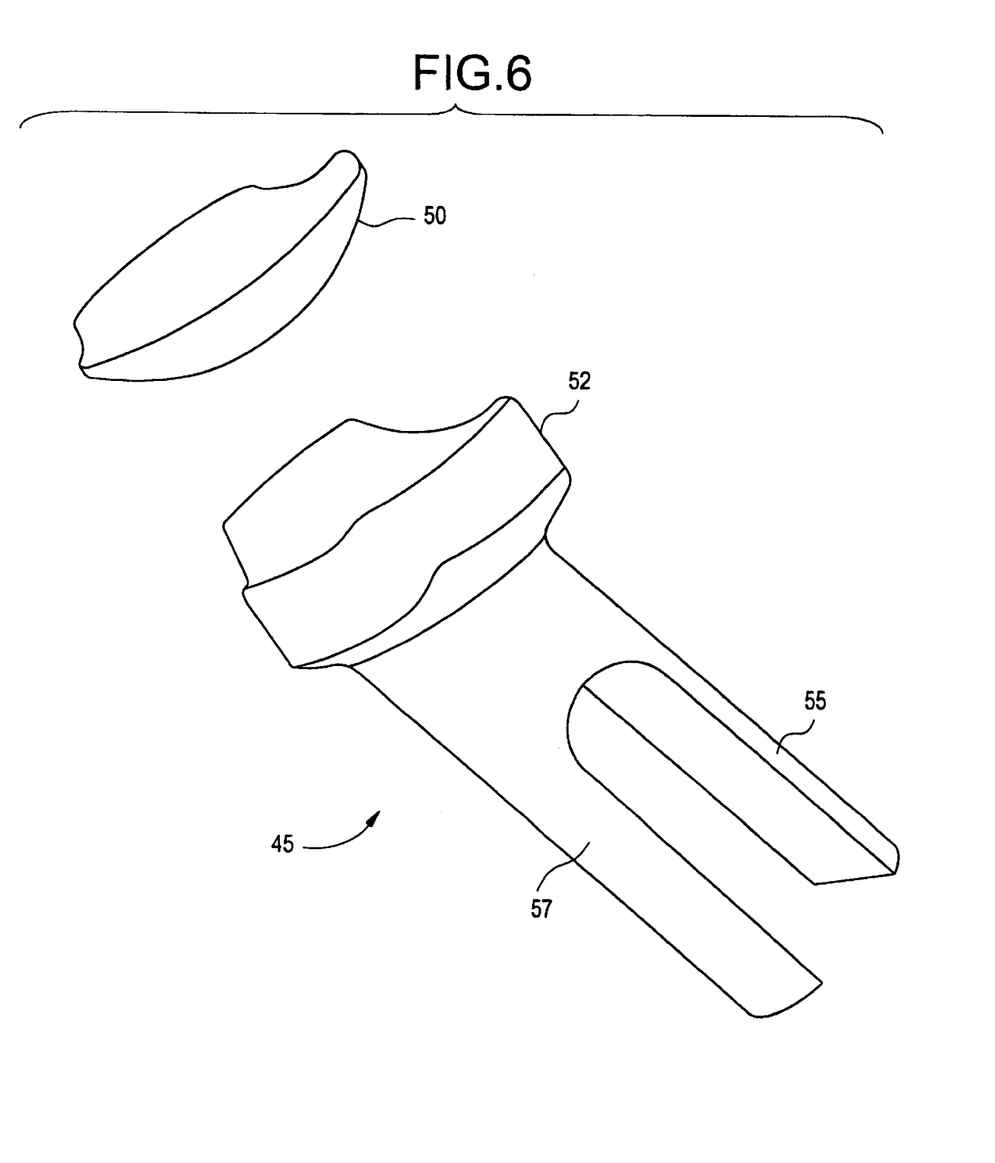
FIG. 6 is a perspective view of the two piece spacing device in accordance with the present invention.

FIG. 6 is a perspective view of the two-piece spacing device 45 in accordance with the present invention. The two pieces include a base 52, having prongs 55, 57 attached thereto and extending therefrom, and a pad 50. Base 52 and prongs 55 and 57 are formed of a single piece, and preferably are formed of a polymer material such as polyethylene. This material is lightweight yet strong enough to support the acetabulum when positioned in place of the removed bone tissue. Further, the polymer material exhibits an indefinite life within the human body. The pad 50 can be formed of numerous materials such as a polymer material, metal alloy or other composite material which is compatible with the human body. As with the base 52 and prongs 55, 57, the pad 50 is of a material which exhibits an indefinite life within the human body. The pad 50 is preferably snap fit within the base 52 so as to allow for the interchangebility of the support structure of the spacer device 45 and the pad 50. However, the pad 50 may alternatively be adhesively secured to the base 52 by use of a suitable adhesive such as polymethylmethacrolate (PMMA).

Figure 6A:
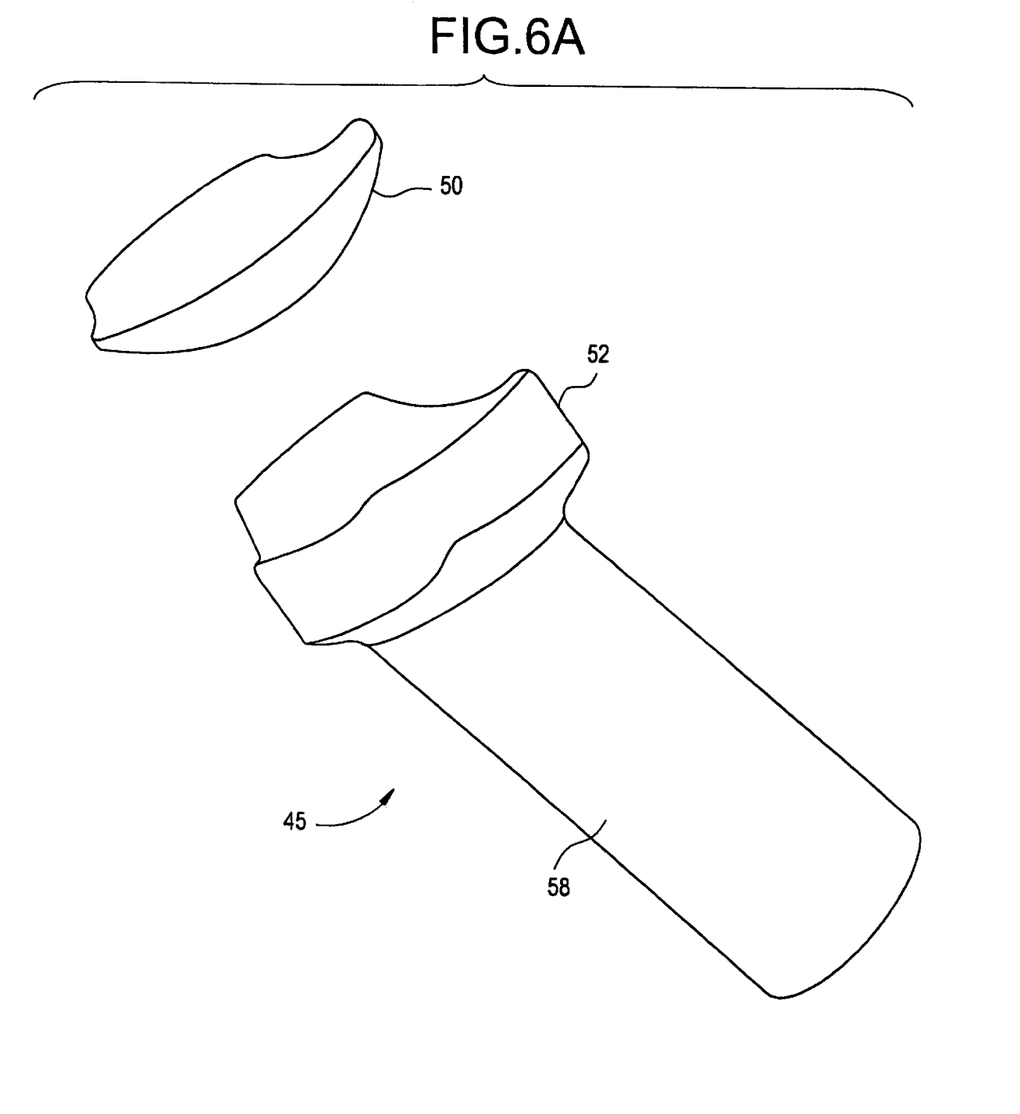
FIG. 6A is a perspective view of a supporting device having the configuration of a stem for insertion into a round bone.

Generally, the spacer device 45 can be supplied in numerous size combinations. These combinations can range in sizes of extra small to extra large with as many as ten or more combinations being available. The proper support structure and pad size for a particular patient and particular joint is determined by trial and error once the diseased bone tissue has been removed. This trial and error process is carried out by use of trial implants which the surgeon positions in place one at a time until the most compatible size is determined. once the proper size is determined, the actual implant to remain in the body is put into place. Again, the above described spacing device can be used in connection with the supporting or numerous joints within the human body with various sizes being provided for all possible joints. Furthermore, while the pelvic bone is a flat bone and a spacing device having prongs to straddle the healthy bone tissue is utilized, when supporting the healthy tissue of a joint such as a knee joint, the supporting structure would take on the configuration of a stem for insertion into a round bone as shown in FIG. 6A, such as a femur and secured using bone cement while the base and pad would take on the contoured configuration of the articular surface to be supported (joint). This is to include joints adjacent long bones such as humerus, femur (knee joint), tibia and radius.

Figure 7:
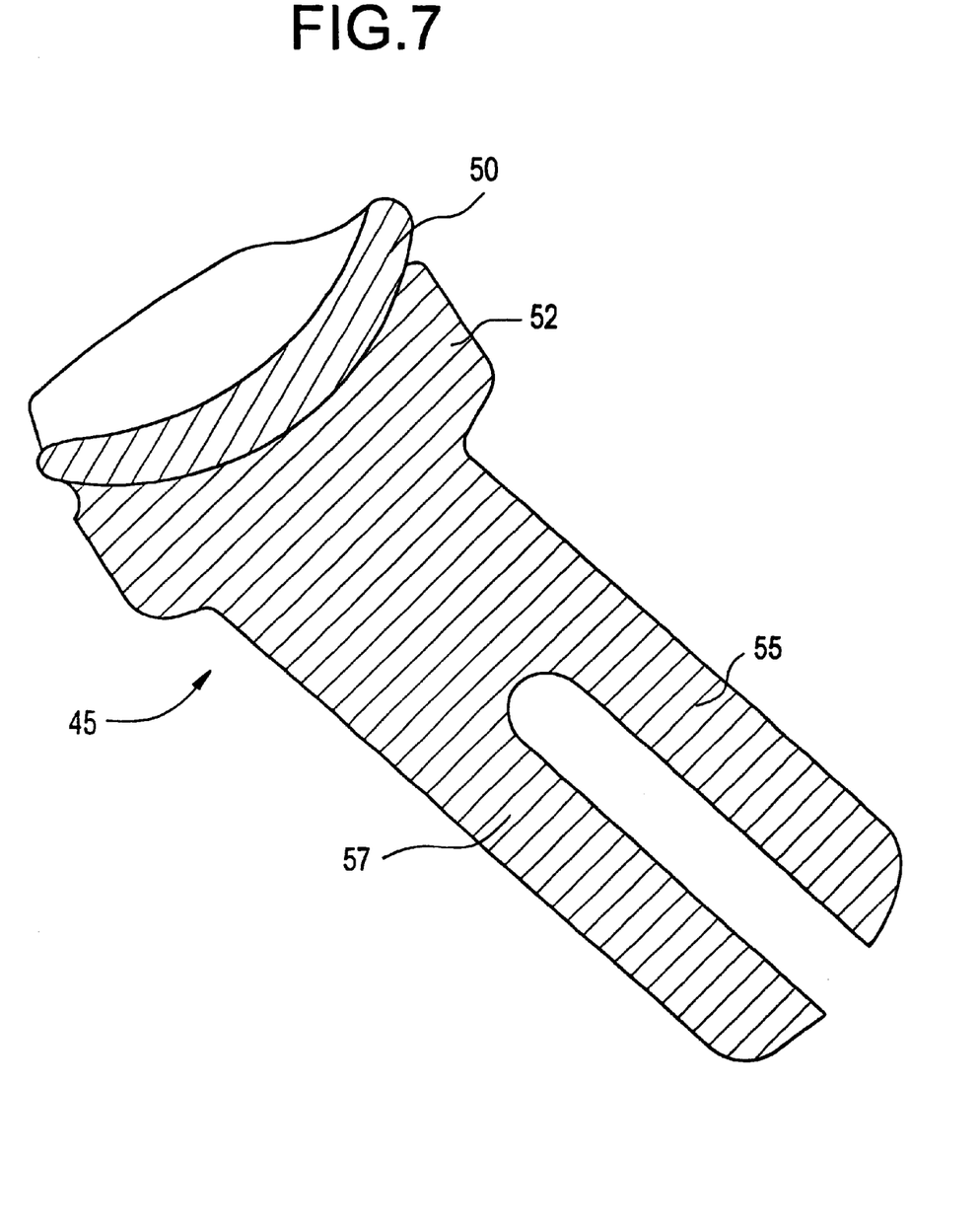
FIG. 7 is a cross sectional view of the assembled spacing device in accordance with the present invention.

FIG. 7 is a cross sectional view of the assembled spacing device 45 in accordance with the present invention. As can be appreciated, the base portion 52 and prongs 55 and 57 are preferably formed of a single structure while the pad 50 is secured thereto in the manner discussed hereinabove.

Figure 8:
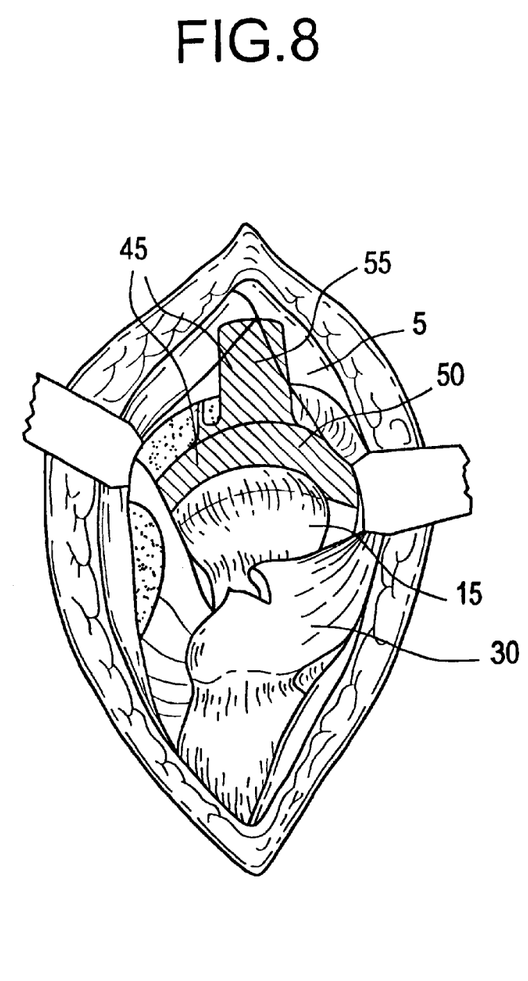
FIG. 8 illustrates the insertion of the spacing device in accordance with the present invention.
Figure 9:
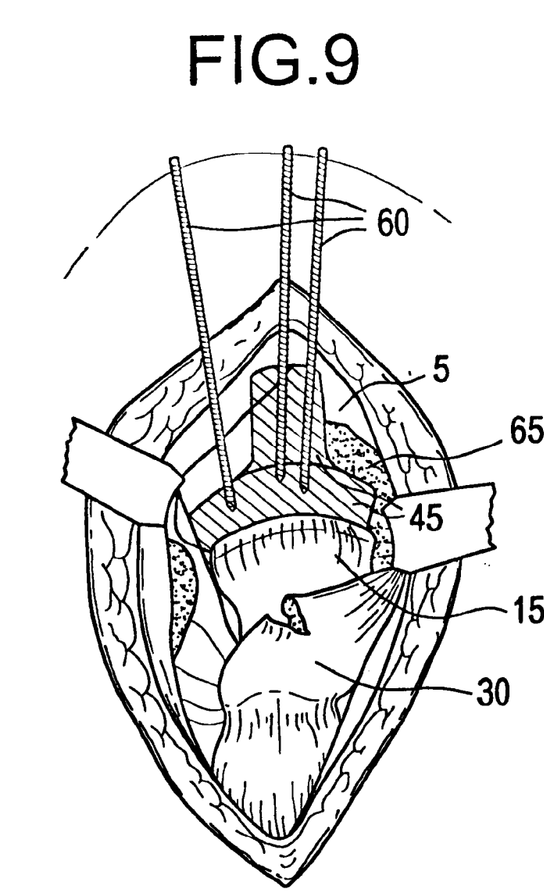
FIG. 9 illustrates the securing of the spacing device in place to support the acetabulum in accordance with the present invention.
Figure 10:
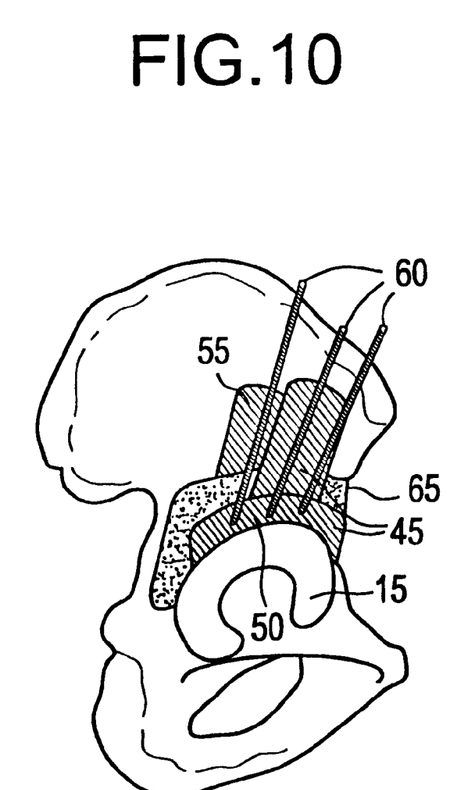
FIG. 10 shows a view of the properly installed spacing device in accordance with the present invention.

Insertion and fixation of the acetabular spacing device 45 is carried out as illustrated in FIGS. 8–10. A properly sized acetabular spacing device 45 is selected for the particular joint of the particular patient, and the appropriately sized acetabular spacing device 45 is then placed into the void 40.

One prong 55 of the acetabular spacing device 45 is placed on the inner table of the iliac crest 5, while the other prong 57 (not illustrated in FIG. 8) of the acetabular spacing device 45 is placed on the outer table of the iliac crest 5.

Once the acetabular spacing device 45 is in place, the device 45 is secured in place. FIG. 9 illustrates the securing of the acetabular spacing device 45 in place to support the acetabulum 15 in accordance with the present invention. After the acetabular spacing device 45 is properly seated, biocompatible screws or pins, such as Steinman pins 60, are retrograded (the heads are installed below the surface) through the ilium 5, and then into the acetabular spacing device 45 for stable fixation. After the pins 60 are in place, the void 40 is reconstructed by filling it with cement, polymethylmethacrylate (PMMA) 65 (commonly known as bone cement). The PMMA 65 fills the void 40 and more fully secures the acetabular spacing device 45 in place by preventing any possible transverse or rotational movement thereof. Finally, the abductor muscle 30 is reattached and a routine standard posterior closure procedure is used to close the incision.

FIG. 10 illustrates a properly installed acetabular spacing device 45 within the ilium 5. Steinman pins 60 hold the prongs 55, 57 of the acetabular spacing device firmly to the ilium 5. As noted hereinabove, bone cement 65 fills the void left after the curetting process to hold the acetabulum spacing device 45 in place and prevent transverse or rotational movement relative to the adjacent bone. The acetabular spacing device pad 50 in accordance with the present invention replaces the previously existing bone tissue and firmly supports the acetabulum 15, which has not been replaced.

As noted hereinabove, in addition to the acetabulum, the device and method of the present invention is adaptable for other ball and socket type joints, such as the shoulder. The device and method are further suitable for use in any situation where diseased, damaged, or necrotic tissue is required to be removed adjacent to a bone joint that is supported by the tissue such that the joint cartilage may remain intact and undisturbed during the surgical procedure.

The acetabular spacing device described herein can be inserted into the body in place of damaged bone tissue to provide underlying support for bone joints, without requiring complete or even partial replacement of the bone joint. Use of the present invention in accordance with the detailed description herein can reduce surgical time for the removal of damaged bone tissue adjacent to a joint previously requiring complete reconstruction of the socket portion of the joint. The present invention can reduce blood loss by up to 80% over the prior art by incorporating the above-noted surgical procedure in place of previously partial or full bone joint reconstruction, and it can decrease a patient's rehabilitation time by eliminating the necessity of partial or full bone joint reconstruction when removing diseased bone tissue adjacent to a joint. Further, this device and process significantly decreases operating time and overall surgical morbidity.

While the present invention has been described with reference to a preferred embodiment, it will be appreciated by those skilled in the art that the invention may be practiced otherwise than as specifically described herein without departing from the spirit and scope of the invention. It is, therefore, to be understood that the spirit and scope of the invention be limited only by the appended claims.

What is claimed is:

1. A bone socket support system for supporting a natural bone socket portion of a bone joint adjacent weak, damaged, or missing tissue, the bone socket support system including a bone socket support comprising:

a support piece forming a first portion of said bone socket support, said support piece having a first end and a second end;

a semi-resilient pad having a smooth concave support surface, said support surface configured to receive and secure to a back surface of the natural bone socket portion, a pad support on the second end of the support piece centrally positioned with respect to said pad for supporting at least a central region of said pad; and securing means for fixedly securing said support piece to health bone tissue;

wherein said bone socket support replaces removed supporting tissue by bridging the void created by the removed tissue and supports the existing natural bone socket portion of the bone joint.

2. The bone socket support system of claim 1, wherein said bone socket support is made of polyethylene.

3. The bone socket support system of claim 1, wherein said securing means comprises biocompatible screws or pins.

4. A bone socket support system for supporting a natural bone socket portion of a bone joint adjacent weak, damaged, or missing tissue, the bone socket support system including a bone socket support comprising:

a semi-resilient pad secured to a first surface of the bone socket support, said pad having a support surface configured to receive and be secured to a back surface of the natural bone socket portion, and a support piece extending from a second surface of the bone socket support fixedly secured to a central region of said second surface of said pad, said support piece including a base portion and a saddle portion configured to straddle healthy bone tissue adjacent the weak, damaged, or missing tissue;

wherein the bone socket support replaces removed supporting tissue by bridging a void created by the removed tissue, supports the existing natural bone socket portion of the bone joint and straddles adjacent healthy bone tissue.

5. A bone socket support system for supporting a natural bone socket portion of a natural bone joint over weak, damaged, or missing tissue, said bone socket support system including a bone socket support comprising:

a support piece having a base portion and a securing portion, said securing portion being in the form of a saddle for straddling healthy bone tissue adjacent the weak, damaged or missing tissue;

a semi-resilient pad fixedly secured to a central region of said base portion, said semi-resilient pad having a support surface configured to receive and be secured to one side of the natural bone socket portion of the natural bone joint;

a fixing means for fixedly connecting said support piece to the healthy bone tissue adjacent the weak, damaged, or missing tissue;

wherein said semi-resilient pad replaces removed supporting tissue by bridging a void created by the removed tissue and supports the existing natural bone socket portion of the natural bone joint and straddles adjacent healthy bone tissue.

6. A bone socket support system for supporting a natural bone socket portion of a bone joint adjacent weak, damaged, or missing tissue, the bone socket support system including a bone socket support comprising:

a support piece forming a first portion of said bone socket support, said support piece having a first end and a second end;

a semi-resilient pad having a smooth concave support surface for receiving and securing to a back surface of the natural bone socket portion, a pad support on the second end of the support stem centrally positioned with respect to said pad for supporting at least a central region of said pad; and securing means comprising biocompatible screws for fixedly securing said support piece to the healthy bone tissue;

wherein said bone socket support replaces removed supporting tissue by bridging the void created by the removed tissue and supports the existing natural bone socket portion of the bone joint.

* * * * *